(12) United States Patent
Manabe et al.

(10) Patent No.: US 8,649,582 B2
(45) Date of Patent: Feb. 11, 2014

(54) PLAQUE REGION EXTRACTING METHOD AND APPARATUS THEREFOR

(75) Inventors: Takahiro Manabe, Yokohama (JP); Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 142 days.

(21) Appl. No.: 13/424,930

(22) Filed: Mar. 20, 2012

(65) Prior Publication Data

US 2012/0243760 A1 Sep. 27, 2012

(30) Foreign Application Priority Data

Mar. 24, 2011 (JP) .................................. 2011-066796

(51) Int. Cl.
*G06K 9/00* (2006.01)
(52) U.S. Cl.
USPC .............................. 382/128; 128/922; 378/4
(58) Field of Classification Search
USPC ................. 382/100, 128, 129, 130, 131, 132; 128/922; 378/4–27
See application file for complete search history.

(56) References Cited

U.S. PATENT DOCUMENTS

| | | | | |
|---|---|---|---|---|
| 4,504,908 A * | 3/1985 | Riederer et al. | ............... | 600/431 |
| 5,768,405 A * | 6/1998 | Makram-Ebeid | ............. | 382/128 |
| 6,678,399 B2 * | 1/2004 | Doi et al. | ....................... | 382/131 |
| 6,765,983 B2 * | 7/2004 | Yan et al. | ............................ | 378/8 |
| 7,283,614 B2 * | 10/2007 | Nakano et al. | ............. | 378/98.12 |
| 7,783,092 B2 * | 8/2010 | Agam et al. | ................... | 382/128 |
| 8,126,241 B2 * | 2/2012 | Zarkh et al. | .................... | 382/131 |
| 8,290,228 B2 * | 10/2012 | Cohen et al. | ................... | 382/128 |
| 8,437,520 B2 * | 5/2013 | Manabe et al. | ................ | 382/128 |
| 2007/0165921 A1 * | 7/2007 | Agam et al. | .................... | 382/128 |
| 2010/0034446 A1 * | 2/2010 | Zhu et al. | ....................... | 382/130 |
| 2012/0148123 A1 * | 6/2012 | Gindele | ........................ | 382/128 |

FOREIGN PATENT DOCUMENTS

JP 2007-275141 10/2007
JP 2009-195561 9/2009

* cited by examiner

*Primary Examiner* — Anand Bhatnagar
(74) *Attorney, Agent, or Firm* — Oblon, Spivak, McClelland, Maier & Neustadt, L.L.P.

(57) ABSTRACT

According to one embodiment, a plaque region extracting apparatus includes a blood vessel wall data extracting unit, an intermediate image data generating unit, an enhancement processing unit, a plaque extracting unit. The blood vessel wall data extracting unit extracts first image data including a blood vessel wall from image data acquired by imaging a subject including blood vessels. The intermediate image data generating unit filters an intermediate region in the first image data to generate intermediate second image data. The enhancement processing unit processes the difference between the first image data and the second image data to generate third image data. The plaque extracting unit extracts a plaque in the blood vessel on the basis of the third image data.

13 Claims, 9 Drawing Sheets

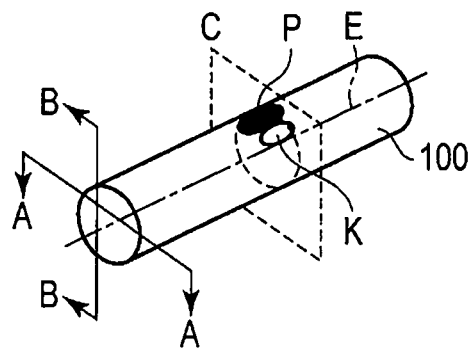
FIG. 3
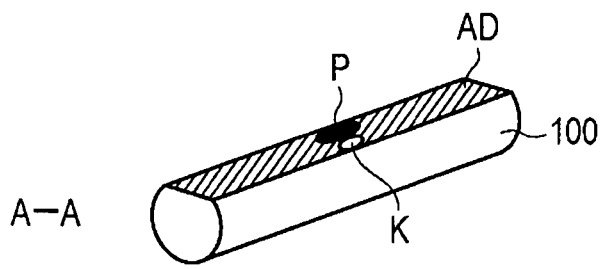
FIG. 4A  A-A
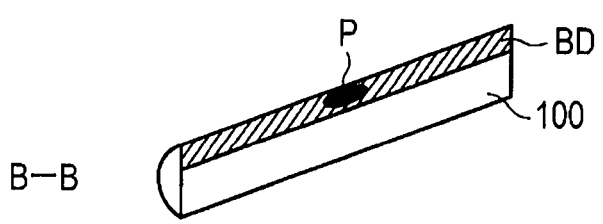
FIG. 4B  B-B
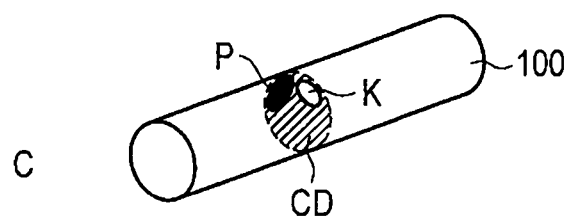
FIG. 4C  C

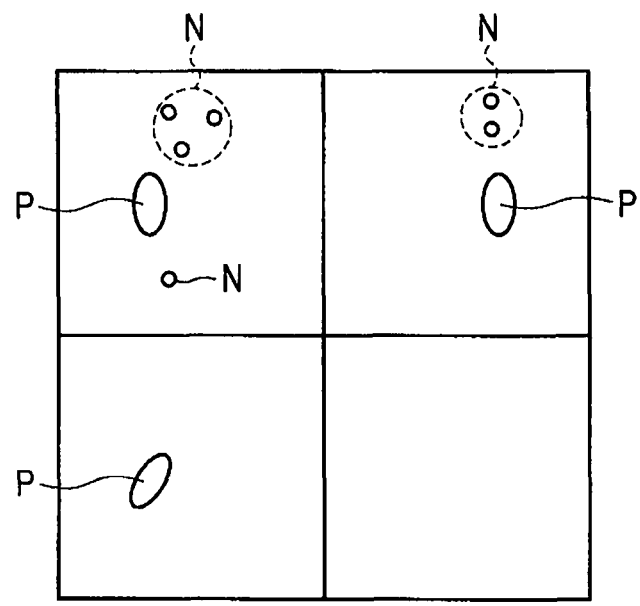
F I G. 11
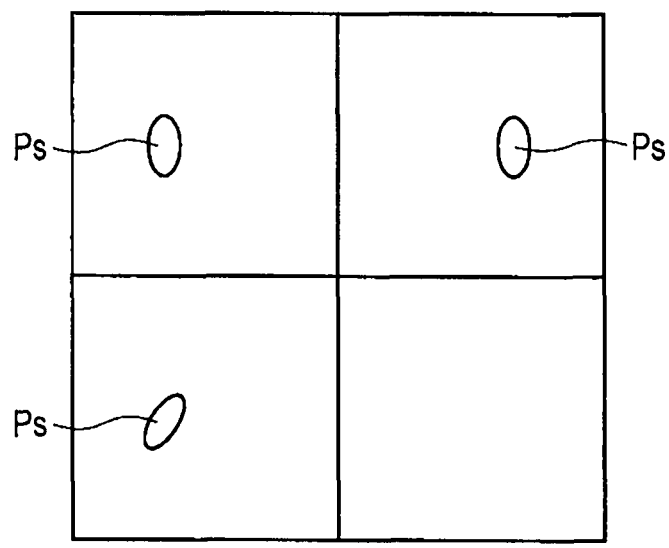
F I G. 12

PLAQUE REGION EXTRACTING METHOD AND APPARATUS THEREFOR

CROSS-REFERENCE TO RELATED APPLICATIONS

This application is based upon and claims the benefit of priority from prior Japanese Patent Application No. 2011-066796, filed Mar. 24, 2011, the entire contents of which are incorporated herein by reference.

FIELD

Embodiments described herein relate generally to a plaque region extracting method and an apparatus therefor for automatically extracting, for example, a plaque region within a blood vessel wall in a CT image.

BACKGROUND

For example, in the diagnosis of coronary arteries, the possibility of cardiac disease associated with plaques in the coronary blood vessel is diagnosed. When broken, the plaques in the coronary blood vessel block or extremely narrow the blood vessel, and induce serious ischemic heart disease. Thus, the coronary arteries are diagnosed. In the coronary artery diagnosis, a narrowed part of the coronary arteries is specified or a plaque in the coronary arteries which has not yet caused the narrowing of a blood vessel is specified from the CT image acquired by X-ray CT scanning. In the coronary artery diagnosis, the plaque amount in a coronary blood vessel wall is measured from a CT image acquired by X-ray CT scanning, and the risk of a coronary disease is diagnosed by the measured plaque amount. Under the present situation, a doctor observes the CT image, and manually extracts plaques, and then diagnoses the risk of a coronary disease in accordance with the amount of extracted plaques. The plaques are extracted by a technique which cuts the CT image by a preset threshold.

BRIEF DESCRIPTION OF THE DRAWINGS

FIG. 3 is a schematic diagram showing sectional directions acquired from coronary artery three-dimensional volume data generated by the medical image processing device;

FIG. 4A is a schematic diagram showing sectional image data AD for the A-A section;

FIG. 4B is a schematic diagram showing sectional image data BD for the B-B section;

FIG. 4C is a schematic diagram showing sectional image data CD for the C section;

FIG. 11 is a diagram showing plaque region candidates and image noises extracted by the image processing unit in the medical image processing device;

FIG. 12 is a diagram showing plaque regions determined by the image processing unit in the medical image processing device;

DETAILED DESCRIPTION

In general, according to one embodiment, a plaque region extracting apparatus includes a blood vessel wall data extracting unit, an intermediate image data generating unit, an enhancement processing unit, and a plaque extracting unit. The blood vessel wall data extracting unit extracts first image data including a blood vessel wall from image data acquired by imaging a subject including blood vessels. The intermediate image data generating unit filters an intermediate region in the first image data to generate intermediate second image data. The enhancement processing unit processes the difference between the first image data and the second image data to generate third image data. The plaque extracting unit extracts a plaque in the blood vessel on the basis of the third image data.

One embodiment of a plaque region extracting apparatus will be hereinafter described with reference to the drawings.

Figure 1:
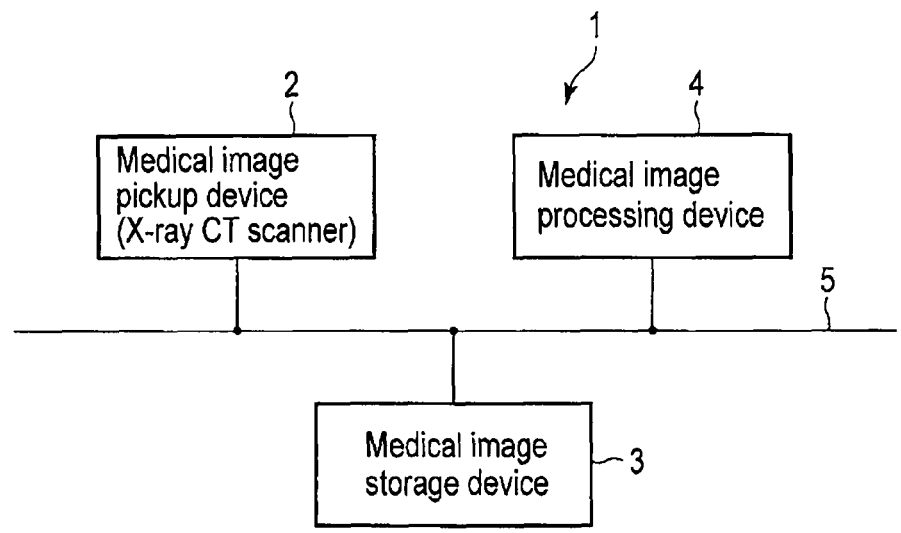
FIG. 1 is a block configuration diagram showing a medical image diagnostic apparatus to which a plaque region extracting apparatus according to one embodiment is applied.

FIG. 1 is a block configuration diagram of a medical image diagnostic apparatus 1 to which the plaque region extracting apparatus is applied. The medical image diagnostic apparatus 1 comprises a medical image pickup device 2, a medical image storage device 3, and a medical image processing device 4. The medical image pickup device 2, the medical image storage device 3, and the medical image processing device 4 are connected to one another, for example, via a local area network (LAN) 5. The medical image pickup device 2 is, for example, an X-ray CT scanner (hereinafter referred to as an X-ray CT scanner 2).

The X-ray CT scanner 2 applies X-rays to a subject, detects the X-rays which have passed through the subject, acquires, for example, three-dimensional (3D) volume data for a CT image of the inside (part of interest) of the subject, and displays the 3D volume data CT image, for example, on a display. Parts of the subject include, for example, the coronary arteries of the heart, the lungs, and the stomach.

The medical image storage device 3 comprises a database. The 3D volume data for CT images acquired by the X-ray CT scanner 2, for example, the 3D volume data for CT images of the coronary arteries of the heart are saved in the medical image storage device 3. The 3D volume data for the CT images saved in the medical image storage device 3 are sent to the medical image processing device 4 via the LAN 5.

The medical image processing device 4 reads the 3D volume data for the CT images saved in the medical image storage device 3, subjects the read 3D volume data to image processing, and automatically extracts a plaque region within a blood vessel wall in the CT image. The extracted image is used to diagnose the possibility of, for example, cardiac disease associated with the plaque in the coronary blood vessel.

Figure 2:
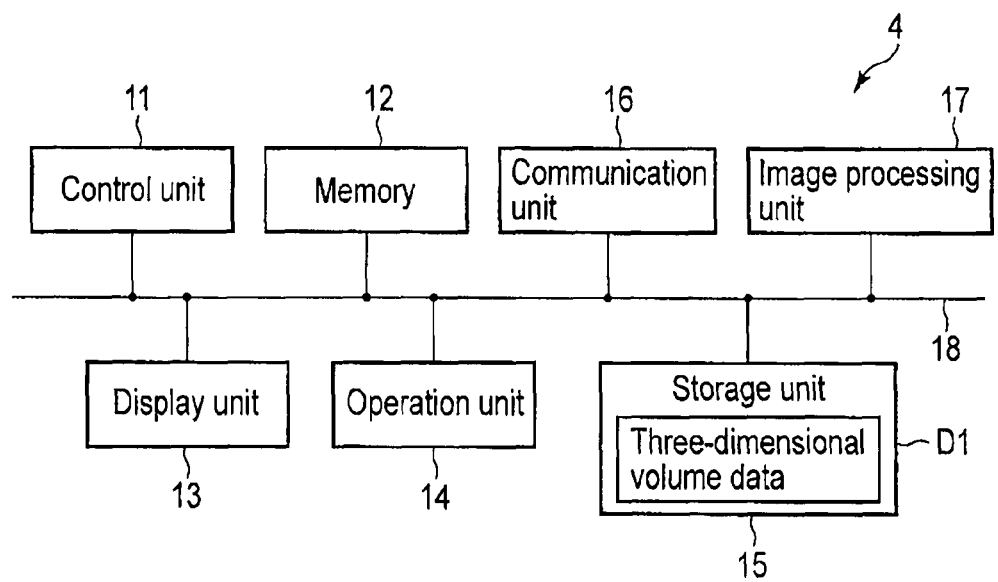
FIG. 2 is a block configuration diagram showing a medical image processing device.

FIG. 2 shows a block configuration diagram of the medical image processing device 4. The medical image processing device 4 comprises a control unit 11 such as a central processing unit (CPU), a memory 12 such as a read only memory (ROM) and a random access memory (RAM), a display unit 13, an operation unit 14, a storage unit 15, and a communication unit 16.

The display unit 13 displays various images such as CT images. The operation unit 14 receives input operation from an operator. An image processing program and various kinds of data are stored in the storage unit 15. The image processing program functions so that the control unit 11 subject the 3D volume data for a CT image acquired by the X-ray CT scanner 2 to image processing and the processed CT image is displayed on the display unit 13. The communication unit 16 communicates with external devices. An image processing unit 17 processes various images of, for example, the 3D volume data for a CT image, and extracts a plaque region from the 3D volume data for the CT image. The control unit 11, the memory 12, the display unit 13, the operation unit 14, the storage unit 15, the communication unit 16, and the image processing unit 17 are electrically connected to one another via a bus line 18.

In addition to the image processing program and the various kinds of data, a plaque region extracting program is stored in the storage unit 15. The plaque region extracting program functions so that the control unit 11 extracts a plaque region from the 3D volume data for the CT image.

The plaque region extracting program is executed by the control unit 11 during the diagnosis of cardiac disease associated with plaques in the coronary blood vessel. The plaque region extracting program includes the following functions: a blood vessel wall data extracting function for extracting first image data for a blood vessel wall from the 3D volume data for the CT image acquired by imaging the subject including coronary blood vessels, an intermediate image data generating function for filtering an intermediate region in the first image data to generate intermediate second image data, an enhancement processing function for generating, from the difference between the first image data and the generated second image data, third image data in which image regions lower in pixel value than peripheral portions in the first image data are enhanced, and a plaque extracting function for finding a standard deviation from the pixel value of the first image data and extracting a plaque, for example, in the coronary arteries in accordance with levels of thresholds based on the standard deviation.

The standard deviation is a statistical analytic value that represents the variation of the pixel value.

The storage unit 15 is, for example, a magnetic disk device or a semiconductor disk device (flash memory).

In accordance with the image processing program and the various kinds of data stored in the storage unit 15, the control unit 11 receives input operation from the operation unit 14, controls, for example, the display unit 13, the communication unit 16, and the image processing unit 17, and subjects the three-dimensional volume data for the CT image to image processing and displays the processed data on the display unit 13.

The control unit 11 executes the plaque region extracting program stored in the storage unit 15. Accordingly, the control unit 11 extracts first blood vessel wall image data from the 3D volume data for the CT image acquired by imaging the subject including coronary blood vessels in the image processing unit 17. The control unit 11 filters an intermediate region in the first image data to generate intermediate second image data. From the difference between the first image data and the second image data, the control unit 11 generates third image data in which image regions lower in pixel value than peripheral portions in the first image data are enhanced. The control unit 11 finds a standard deviation from the pixel value of the first image data, and extracts a plaque, for example, in the coronary arteries in accordance with levels of thresholds based on the standard deviation.

For example, a startup program to be executed by the control unit 11 is stored in the memory 12. The memory 12 also functions as a work area of the control unit 11. The startup program is read and executed by the control unit 11 at the startup of the medical image processing device 4.

The display unit 13 displays various images such as 2D images and 3D images in color. The display unit 13 is, for example, a liquid crystal display or a CRT display.

The operation unit 14 is operated by the operator for inputting. The operation unit 14 receives various input operations including, for example, the start of image display, the switch of images, and the change of settings. The operation unit 14 is an input device such as a mouse or a keyboard.

The communication unit 16 communicates with external devices via the LAN 5, and is, for example, a LAN card or a modem. The external devices are, for example, the medical image pickup device 2 and the medical image storage device 3.

The image processing unit 17 executes the plaque region extracting program stored in the storage unit 15, and extracts, for example, a plaque in the coronary blood vessel from the 3D volume data for the CT image.

More specifically, the image processing unit 17 functions as a plaque extracting device, and reads the 3D volume data for the CT image saved in the medical image storage device 3, for example, heart volume data. The image processing unit 17 uses the 3D volume data to cut out a region of interest, for example, a part of the coronary arteries from the read heart volume data. The image processing unit 17 extracts the center line of the coronary blood vessel from the cut coronary artery 3D volume data, and extracts first blood vessel wall image data from the coronary artery 3D volume data along the direction of the extracted center line. The image processing unit 17 filters an intermediate region in the extracted first image data to generate intermediate second image data. From the difference between the first image data and the second image data, the image processing unit 17 generates third image data in which image regions lower in pixel value than peripheral portions in the first image data are enhanced. The image processing unit 17 finds a standard deviation from the pixel value of the third image data, and extracts a plaque, for example, in the coronary arteries in accordance with levels of thresholds based on the standard deviation.

The image processing unit 17 generates curved planer reconstruction (CPR) images of sections from the cut coronary artery 3D volume data. The CPR images are, for example, slice images of image data for an A-A section, a B-B section, and a C section of a coronary blood vessel 100, for example, as shown in FIG. 3. The A-A section is a section along the direction of a center line (blood flow direction) E of the blood vessel 100. The B-B section is a section which extends along the direction of the center line E of the blood vessel 100 and which is perpendicular to the A-A section. The C section is a section perpendicular to the direction of the center line E of the blood vessel 100.

Figure 5:
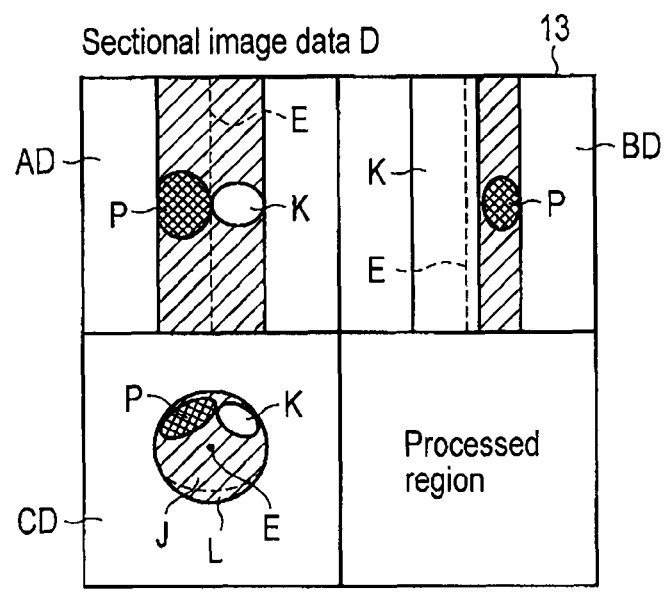
FIG. 5 is a diagram showing an example of how to display the sectional image data for the coronary artery three-dimensional volume data acquired by the medical image processing device.

FIG. 4A shows a schematic diagram of sectional image data AD for the A-A section. FIG. 4B shows a schematic diagram of sectional image data BD for the B-B section. FIG. 4C shows a schematic diagram of sectional image data CD for the C section. FIG. 5 shows an example of how to display, on the display unit 13, the sectional image data AD for the A-A section, the sectional image data BD for the B-B section, and the sectional image data CD for the C section. FIG. 3 to FIG. 5 shows a plaque P and a calcified part K in the blood vessel 100. J indicates a lumen, and L indicates a wall.

Figure 6:
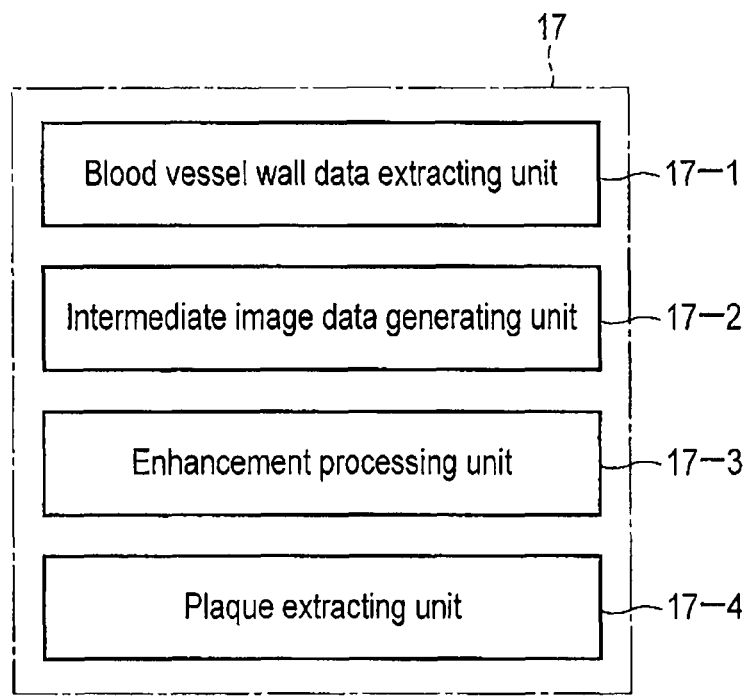
FIG. 6 is a specific functional block diagram showing an image processing unit in the medical image processing device.

FIG. 6 shows a specific functional block diagram in the image processing unit 17. The image processing unit 17 comprises a blood vessel wall data extracting unit 17-1, an intermediate image data generating unit 17-2, an enhancement processing unit 17-3, and a plaque extracting unit 17-4.

The blood vessel wall data extracting unit 17-1 cuts out, for example, a portion of the coronary arteries from CT image heart volume data D shown in FIG. 5 in the form of 3D volume data, and extracts two-dimensional (2D) image data (first image data) W for the coronary blood vessel wall from the 3D volume data.

Figure 7:
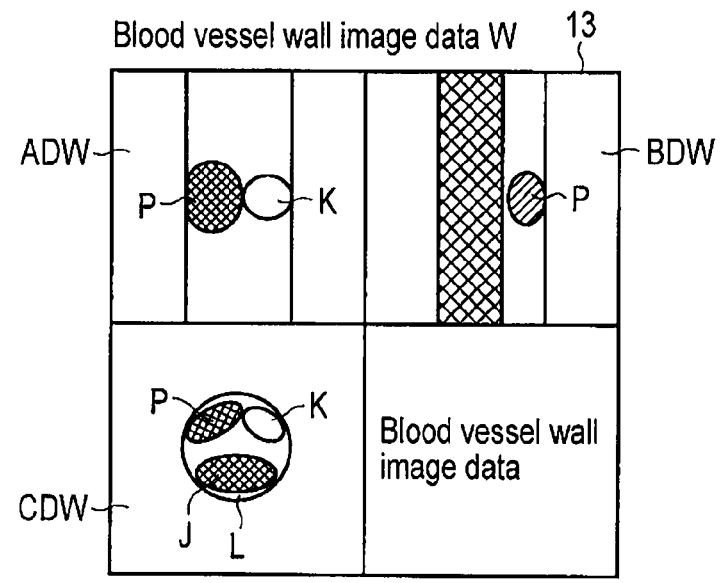
FIG. 7 is a diagram showing an example of how two-dimensional first image data for a blood vessel wall is displayed by the image processing unit in the medical image processing device.

FIG. 7 shows an example of how the blood vessel wall image data W is displayed. ADW indicates blood vessel wall image data in the sectional image data AD for the A-A section shown in FIG. 5. BDW indicates blood vessel wall image data in the sectional image data BD for the B-B section shown in FIG. 5. CDW indicates blood vessel wall image data in the sectional image data BD for the C section shown in FIG. 5.

Figure 8:
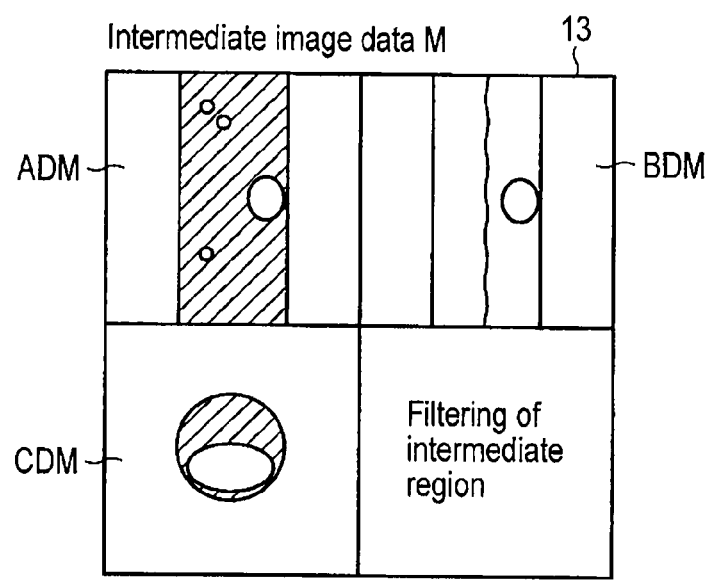
FIG. 8 is a diagram showing intermediate image data generated by filtering an intermediate region in the image processing unit in the medical image processing device.

The intermediate image data generating unit 17-2 filters the intermediate region in the image data W for the coronary blood vessel wall, for example, in the blood vessel wall image data ADW corresponding to the A-A section, the blood vessel wall image data BDW corresponding to the B-B section, and the blood vessel wall image data CDW corresponding to the C section that are shown in FIG. 7, thereby generating intermediate image data (second image data) M, for example, shown in FIG. 8.

The intermediate region filtering includes the filtering of the intermediate region for all the regions of CT values of the blood vessel wall image data ADW, BDW, and CDW along the center line of the blood vessel 100 in the blood vessel wall image data ADW, BDW, and CDW. For example, a median filter is used for the filtering of the intermediate region.

In FIG. 8, ADM indicates intermediate image data in which the blood vessel wall image data ADW shown in FIG. 7 is filtered. BDM indicates intermediate image data in which the blood vessel wall image data BOW shown in FIG. 7 is filtered. CDM indicates intermediate image data in which the blood vessel wall image data CDW shown in FIG. 7 is filtered.

The enhancement processing unit 17-3 generates differential image data (third image data) S in which image regions lower in pixel value than the peripheral portions are enhanced in accordance with the difference between the blood vessel wall image data ADW, BDW, and CDW shown in FIG. 7 and the intermediate image data ADM, BDM, and CDM shown in FIG. 8.

More specifically, the enhancement processing unit 17-3 finds a difference of CT values between the blood vessel wall image data ADW, BDW, and CDW shown in FIG. 7 and the intermediate image data ADM, BDM, and CDM shown in FIG. 8. From the found difference, the enhancement processing unit 17-3 generates the differential image data S shown in FIG. 9 in which the image regions lower in CT value than the peripheral portions are enhanced. From the generated differential image data S, the enhancement processing unit 17-3 generates a differential value distribution (histogram) H shown in FIG. 10 that indicates the number of pixels versus the difference of CT values.

Figure 9:
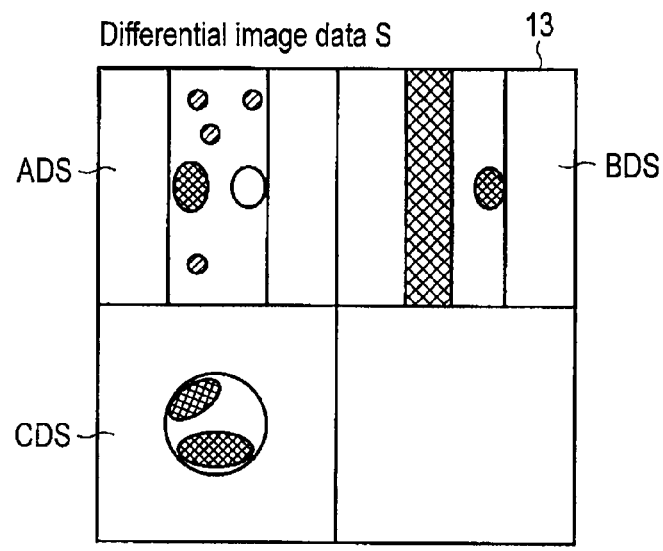
FIG. 9 is a schematic diagram showing differential image data obtained by image processing in the image processing unit in the medical image processing device.

In the differential image data S shown in FIG. 9, ADS indicates differential image data between the blood vessel wall image data ADW shown in FIG. 7 and the intermediate image data ADM shown in FIG. 8. BDS indicates differential image data between the blood vessel wall image data BDW shown in FIG. 7 and the intermediate image data BDM shown in FIG. 8. CDS indicates differential image data between the blood vessel wall image data CDW shown in FIG. 7 and the intermediate image data CDM shown in FIG. 8.

Figure 10:
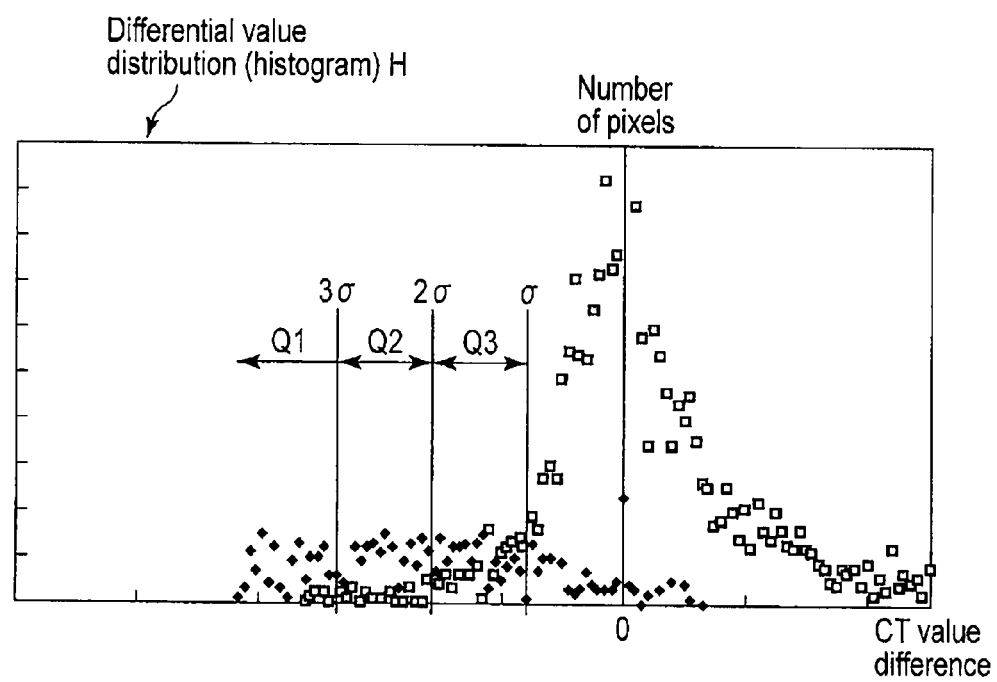
FIG. 10 is a graph showing a differential value distribution generated by the image processing unit in the medical image processing device.

The differential value distribution H shown in FIG. 10 indicates the number of pixels versus the difference of CT values between the blood vessel wall image data ADW, BOW, and CDW shown in FIG. 7 and the intermediate image data ADM, BDM, and CDM shown in FIG. 8. The difference of CT values is obtained, for example, by finding, over the entire image, the difference of CT values for the same coordinates of the blood vessel wall image data ADW and the intermediate image data ADM. The difference of CT values may otherwise be obtained from the number of pixels versus the difference of CT values between the blood vessel wall image data BDW and the intermediate image data BDM, or from the number of pixels versus the difference of CT values between the blood vessel wall image data CDW and the intermediate image data CDM.

The plaque extracting unit 17-4 finds an image noise standard deviation $\sigma$ from CT values in a required part of the blood vessel 100, for example, the beginning of the aorta. The plaque extracting unit 17-4 calculates thresholds $-\sigma$, $-2\sigma$, and $-3\sigma$ by integrally multiplying levels of thresholds based on the found standard deviation $\sigma$, for example, the standard deviation $\sigma$ by different numerical values. The plaque extracting unit 17-4 separates the difference of CT values in accordance with regions that can be sorted by the thresholds $-\sigma$, $-2\sigma$, and $-3\sigma$, thereby determining the certainty factor of the plaque region. The standard deviation $\sigma$ of the image noise is found from the beginning of the aorta because the beginning of the aorta has a large volume and objects equal in CT value gather therein.

More specifically, the plaque extracting unit 17-4 sets the thresholds $-\sigma$, $-2\sigma$, and $-3\sigma$, and unconditionally determines, as the plaque region, a difference of CT values equal to or more than the threshold $-3\sigma$, that is, a difference of CT values included in a judgment range Q1 of the CT values equal to or less than the threshold $-3\sigma$ shown in FIG. 10.

The plaque extracting unit 17-4 determines, as the plaque region with a first condition, the difference of CT values included in a judgment range Q2 between the threshold $-3\sigma$ and the threshold $-2\sigma$. The first condition is to be adjacent to the plaque region which is unconditionally determined from the difference of CT values between the threshold $-3\sigma$ and the threshold $-2\sigma$. Alternatively, the first condition is that an image portion in the coronary artery 3D volume data shown in FIG. 5 corresponding to the difference of CT values included in the judgment range Q2 has a given volume, for example, of 0.12 mm$^3$ or more.

In order to make a judgment with the first condition, the plaque extracting unit 17-4 labels the image portion corresponding to the difference of CT values included in the judgment range Q2, for example, the image portion in the three-dimensional volume data for the coronary arteries shown in FIG. 5.

The plaque extracting unit 17-4 determines, as the plaque region with a second condition, the difference of CT values included in the judgment range Q3 between the threshold $-2\sigma$ and the threshold $-\sigma$. The second condition is to be adjacent to the plaque region which is determined as described above.

In order to make a judgment with the second condition, the plaque extracting unit 17-4 labels the image portion corresponding to the difference of CT values included in the judgment range Q3, for example, the image portion in the three-dimensional volume data for the coronary arteries shown in FIG. 5.

When determining the certainty factor of the plaque region on the basis of the difference of CT values of the judgment ranges Q1, Q2, and Q3, the plaque extracting unit 17-4 excludes plaques having a wall thickness of a given value, for example, less than 1 mm, and also excludes outermost pixels in the wall. In other words, when determining the certainty factor of the plaque region on the basis of the difference of CT values of the judgment ranges Q1, Q2, and Q3, the plaque extracting unit 17-4 extracts plaques having a wall thickness of a given value, for example, 1 mm or more, and does not extract plaques in the outermost pixels in the wall.

FIG. 11 shows plaque region candidates P and image noises N extracted by the threshold $-\sigma$ from the differential image data S shown in FIG. 9.

FIG. 12 shows results obtained by setting the thresholds $-\sigma$, $-2\sigma$, and $-3\sigma$ in the plaque extracting unit 17-4, separating the difference of CT values in accordance with the judgment ranges Q1, Q2, and Q3 that can be sorted by the thresholds $-\sigma$, $-2\sigma$, and $-3\sigma$, and thereby determining plaques Ps from the plaque region candidates P.

Now, the plaque extracting operation by the apparatus having such a configuration is described.

The X-ray CT scanner 2 applies X-rays to a subject such as a human body to which a contrast media is injected, detects the X-rays which have passed through the subject, acquires, for example, 3D volume data for a CT image of a part of interest of the subject such as the coronary arteries of the heart, and displays the 3D volume data CT image, for example, on the display.

The medical image storage device 3 stores, in the database, the 3D volume data for CT images acquired by the X-ray CT scanner 2, for example, the 3D volume data for CT images of the coronary arteries of the heart. The 3D volume data for the CT images saved in the medical image storage device 3 is sent to the medical image processing device 4 via the LAN 5.

The medical image processing device 4 reads the 3D volume data for the CT images saved in the medical image storage device 3, subjects the 3D volume data to image processing, and automatically extracts a plaque region within a blood vessel wall in the CT image. The image of the extracted plaque region is used to diagnose the possibility of, for example, cardiac disease associated with the plaque in the coronary blood vessel.

As basic processing, the image processing unit 17 subjects the 3D volume data for the heart to image cutting processing, calcification extracting processing, lumen (contrast media) extracting processing, external wall extracting processing, and plaque extracting processing.

More specifically, the image processing unit 17 reads the 3D volume data for the CT image saved in the medical image storage device 3, for example, heart volume data. The image processing unit 17 cuts out 3D volume data for a region of interest, for example, a part of the coronary arteries from the heart volume data.

The image processing unit 17 acquires, for example, a CT value of the beginning of the aorta from the volume data for the coronary arteries, and extracts, as calcification (calcified plaque), a region having a CT value which is more than 1.2 times the CT value of the beginning of the aorta. In this case, the image processing unit 17 uses the fact that the CT value of the calcification is higher than the CT value of the contrast media, in particular, uses the CT value of the beginning of the aorta having a low partial volume effect.

From the 3D volume data for the cut part of the coronary arteries, the image processing unit 17 generates CPR images of sections, for example, the sectional image data AD for the A-A section, the sectional image data BD for the B-B section, and the sectional image data CD for the C section shown in FIG. 5. The image processing unit 17 sets a tube ROI (three-dimensional region of interest) around the center line from the sectional image data AD, BD, and CD, and extracts and removes calcification in this tube ROI.

The image processing unit 17 digitizes, for example, the sectional image data CD shown in FIG. 5, and scans in a direction toward the internal wall of the coronary blood vessel. The image processing unit 17 finds the center of gravity within the coronary blood vessel from the scanning results, and finds the center point of the coronary blood vessel based on the center of gravity.

The image processing unit 17 scans in the extending directions of the coronary blood vessels to generate sectional image data CD, and finds the center points of the coronary blood vessel from the sectional image data CD.

The image processing unit 17 finds a center line E of the coronary blood vessel by connecting the center points.

Figure 13:
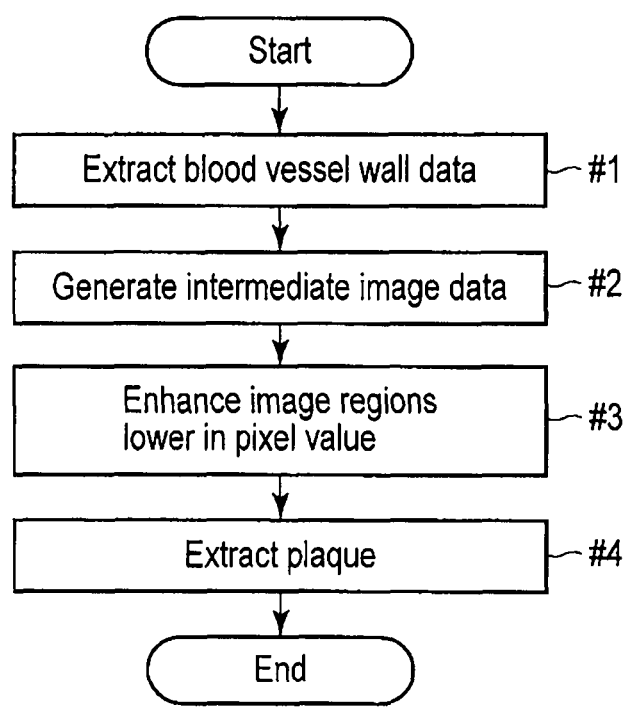
FIG. 13 is a flowchart for plaque region extraction in the medical image processing device.
Figure 14:
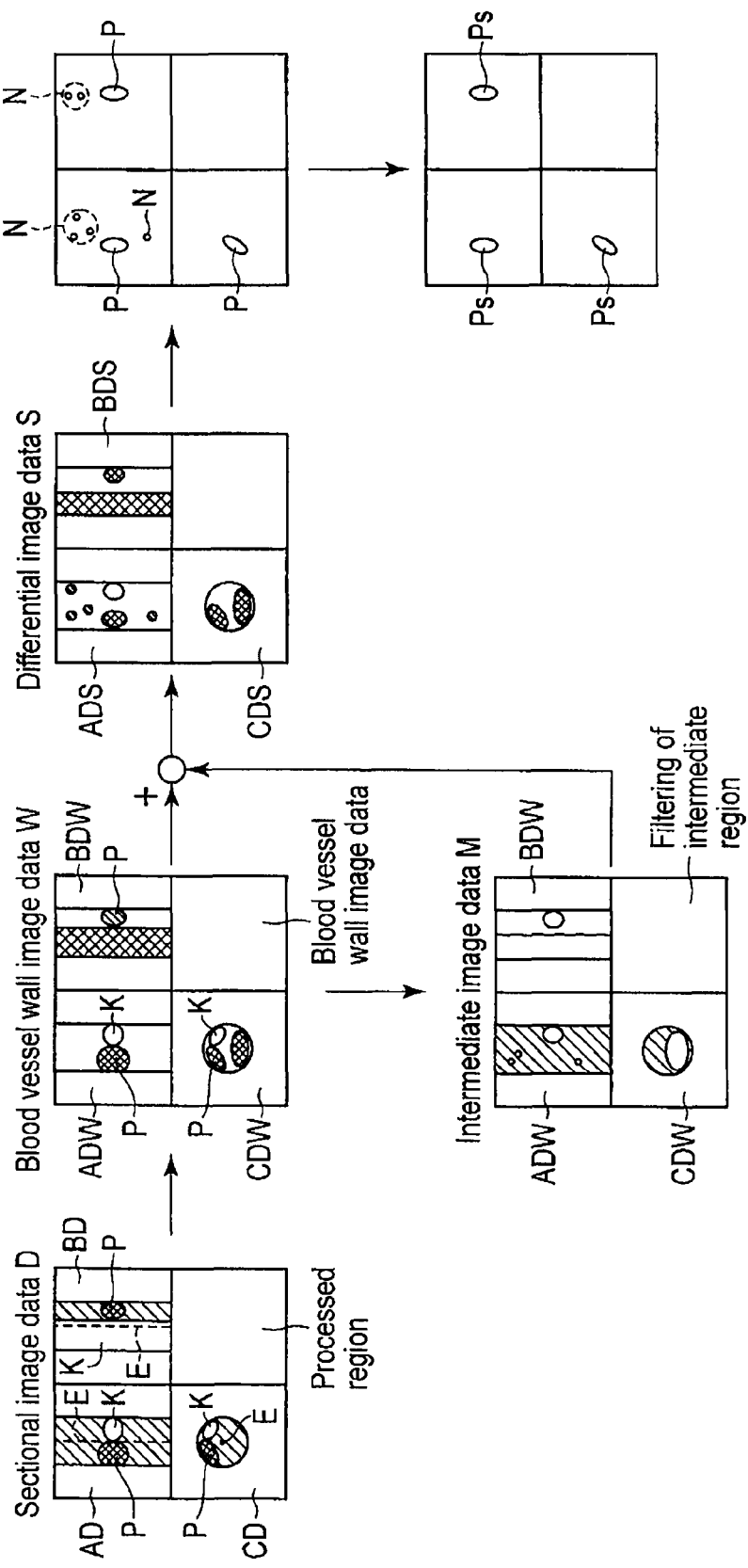
FIG. 14 is a diagram showing the flow of image data processing in the plaque region extraction operation by the medical image processing device.

The plaque region extraction operation is described below with reference to a plaque region extracting flowchart shown in FIG. 13. FIG. 14 shows the flow of image data processing in the plaque region extraction operation.

In step #1, the blood vessel wall data extracting unit 17-1 cuts out, for example, a portion of the coronary arteries from the CT image heart volume data D shown in FIG. 5 in the form of 3D volume data. From the cut 3D volume data, the blood vessel wall data extracting unit 17-1 extracts 2D image data W for the coronary blood vessel wall shown in FIG. 7, that is, the blood vessel wall image data ADW, BDW, and CDW.

In step #2, the intermediate image data generating unit 17-2 filters the intermediate region in the image data W for the coronary blood vessel wall, for example, in the blood vessel wall image data ADW, BDW, and CDW shown in FIG. 7 along the direction of the center line E of the blood vessel 100, thereby generating the intermediate image data M, for example, shown in FIG. 8. For example, the median filter is used for the filtering of the intermediate region.

In step #3, the enhancement processing unit 17-3 finds a difference of CT values between the blood vessel wall image data ADW, BDW, and CDW shown in FIG. 7 and the intermediate image data ADM, BDM, and CDM shown in FIG. 8. From the found difference, the enhancement processing unit 17-3 generates the differential image data S shown in FIG. 9 in which the image regions lower in pixel value than the peripheral portions are enhanced. The differential image data S is generated by subtracting the intermediate image data ADM, BDM, and CDM shown in FIG. 8 from the blood vessel wall image data ADW, BDW, and CDW shown in FIG. 7, respectively.

From the differential image data S, the enhancement processing unit 17-3 generates the differential value distribution H shown in FIG. 10 that indicates the number of pixels versus the difference of CT values.

In step #4, the plaque extracting unit 17-4 finds the image noise standard deviation σ from CT values in a required part of the blood vessel 100, for example, the beginning of the aorta. The plaque extracting unit 17-4 calculates the thresholds −σ, −2σ, and −3σ by integrally multiplying levels of thresholds based on the standard deviation σ, for example, the standard deviation σ by different numerical values, respectively. The plaque extracting unit 17-4 separates the difference of CT values in accordance with regions that can be sorted by the thresholds −σ, −2σ, and −3σ, thereby determining the certainty factor of the plaque region.

More specifically, the plaque extracting unit 17-4 unconditionally determines, as the plaque region, the difference of CT values equal to or more than the threshold −3σ in the differential value distribution H shown in FIG. 10, that is, the difference of CT values included in the judgment range Q1 of the CT values equal to or less than the threshold −3σ shown in FIG. 10.

The plaque extracting unit 17-4 determines, as the plaque region with a first condition, the difference of CT values included in the judgment range Q2 between the threshold −3σ and the threshold −2σ. The first condition is to be adjacent to the plaque region which is unconditionally determined from the difference of CT values between the threshold −3σ and the threshold −2σ. Alternatively, the first condition is that an image portion in the coronary artery 3D volume data shown in FIG. 5 corresponding to the difference of CT values included in the judgment range Q2 has a given volume, for example, of 0.12 mm³ or more.

The plaque extracting unit 17-4 determines, as the plaque region with a second condition, the difference of CT values included in the judgment range Q3 between the threshold −2σ and the threshold −σ. The second condition is to be adjacent to the already determined plaque region.

When determining the certainty factor of the plaque region on the basis of the difference of CT values of the judgment ranges Q1, Q2, and Q3, the plaque extracting unit 17-4 excludes plaques having a wall thickness of a given value, for example, less than 1 mm, and also excludes outermost pixels in the wall. In other words, when determining the certainty factor of the plaque region on the basis of the difference of CT values of the judgment ranges Q1, Q2, and Q3, the plaque extracting unit 17-4 extracts plaques having a wall thickness of a given value, for example, 1 mm or more, and does not extract plaques in the outermost pixels in the wall.

As a result of the plaque extraction, the plaque Ps is determined from the plaque region candidates P, as shown in FIG. 12. It is apparent from the contrast with the result of extraction using the threshold −σ shown in FIG. 11 that the determined plaque Ps are free of the image noises N, and the plaques Ps having high accuracy are only extracted.

Simulation results of the plaque extraction operation by the present device is described.

Figure 15:
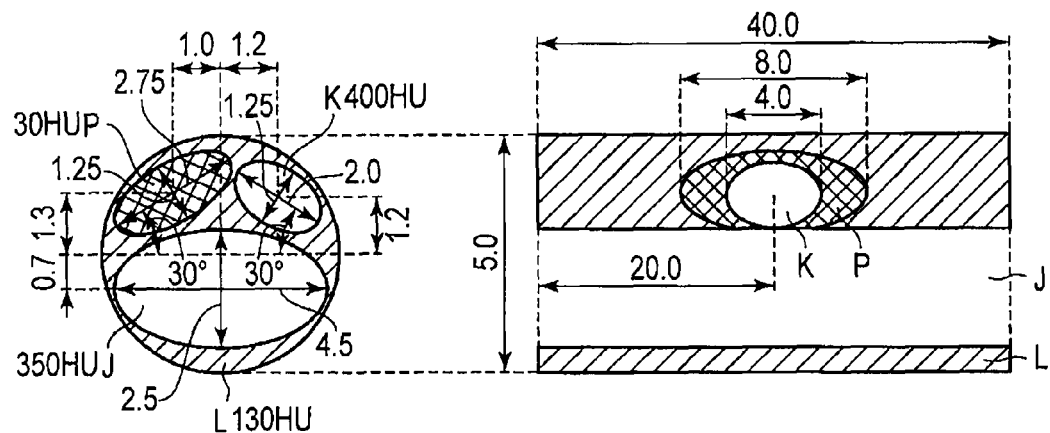
FIG. 15 is a diagram showing an example of a simulation model of the plaque extraction in the medical image processing device.

A numerical phantom shown in FIG. 15 is used in the plaque extraction simulation. There are numerical phantoms without image noises and with image noises. The threshold is, for example, 60 HU. The plaque P is at, for example, 30 HU. The calcified part K is at 400 HU. The lumen J is at 350 HU. The wall L is at 130 HU.

Figure 16A:
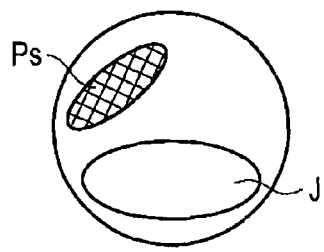
FIG. 16A is a diagram showing simulation results of the plaque extraction in the medical image processing device.
Figure 16B:
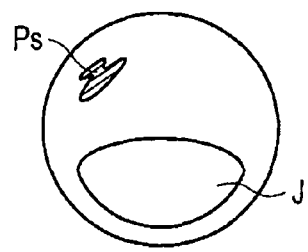
FIG. 16B is a diagram showing simulation results of the plaque extraction in the medical image processing device.

A simulator reconstructs an image from the numerical phantom to generate raw data for the coronary blood vessel, and uses this raw data to run the plaque extraction simulation. As a result of the simulation, the plaque Ps can be extracted, for example, as shown in FIG. 16A and FIG. 16B. FIG. 16A includes no image noises. FIG. 16B includes image noises.

Thus, according to the embodiment described above, the blood vessel wall image data W are extracted, for example, from the coronary artery 3D volume data cut out from the CT image heart volume data D. The intermediate regions in the blood vessel wall image data W are filtered to generate the intermediate image data M. The differential image data S in which the image regions lower in CT value than the peripheral portions are enhanced is generated from the difference of CT values between the blood vessel wall image data W and the intermediate image data M. The differential value distribution H that indicates the number of pixels versus the difference of CT values is generated from the differential image data S, and the thresholds −σ, −2σ, and −3σ are calculated from the image noise standard deviation σ found from CT values in, for example, the beginning of the aorta. The difference of CT values is separated in accordance with regions that can be sorted by the thresholds −σ, −2σ, and −3σ, and the certainty factor of the plaque region is thereby determined. This ensures that the plaque Ps can be extracted, and regions other than the plaque Ps are not extracted as plaques. Thus, the extracted plaques can be matched to the plaques in the coronary blood vessel wall extracted by doctor's interpretation.

In the plaque extraction, the difference of CT values included in the judgment range Q1 of the CT value difference equal to or less than the threshold −3σ in the differential value distribution H shown in FIG. 10 is unconditionally determined as the plaque region. The difference of CT values included in the judgment range Q2 between the threshold −3σ and the threshold −2σ is determined as the plaque region with the first condition. The difference of CT values included in the judgment range Q3 between the threshold −2σ and the threshold −σ is determined as the plaque region with the second condition. This allows higher accuracy of the extraction of the plaque Ps.

The accuracy of the extraction of the plaque Ps can also be increased by excluding plaques having a wall thickness of a given value, for example, less than 1 mm and also excluding the outermost pixels in the wall in the difference of CT values of the judgment ranges Q1, Q2, and Q3.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A plaque region extracting method comprising:
    extracting first image data including a blood vessel wall from image data acquired by imaging a subject including blood vessels;
    filtering an intermediate region in the first image data to generate intermediate second image data;
    processing the difference between the first image data and the second image data to generate third image data; and
    extracting a plaque in the blood vessel on the basis of the third image data.

2. The plaque region extracting method according to claim 1, wherein the second image data is generated by filtering the first image data along the traveling direction of the blood vessel to find the value of the intermediate region.

3. The plaque region extracting method according to claim 1, wherein
the third image data is generated from the difference between the first image data and the second image data by enhancing image regions lower in pixel value than peripheral portions in the first image data.

4. The plaque region extracting method according to claim 1, wherein
the plaque is extracted from the blood vessel in accordance with levels of thresholds based on a standard deviation which is found from the pixel value of the first image data.

5. A plaque region extracting apparatus comprising:
a blood vessel wall data extracting unit which extracts first image data including a blood vessel wall from image data acquired by imaging a subject including blood vessels;
an intermediate image data generating unit which filters an intermediate region in the first image data to generate intermediate second image data;
an enhancement processing unit which processes the difference between the first image data and the second image data to generate third image data; and
a plaque extracting unit which extracts a plaque in the blood vessel on the basis of the third image data.

6. The plaque region extracting apparatus according to claim 5, wherein
the intermediate image data generating unit generates the second image data by filtering the first image data along the traveling direction of the blood vessel to find the value of the intermediate region.

7. The plaque region extracting apparatus according to claim 5, wherein
the enhancement processing unit generates the third image data from the difference between the first image data and the second image data by enhancing image regions lower in pixel value than peripheral portions in the first image data.

8. The plaque region extracting apparatus according to claim 5, wherein
the plaque extracting unit extracts the plaque from the blood vessel in accordance with levels of thresholds based on a standard deviation which is found from the pixel value of the first image data.

9. The plaque region extracting apparatus according to claim 5, wherein
the image data is CT image data, and
the plaque extracting unit finds a standard deviation of CT values from a required part of the blood vessel, multiplies the standard deviation by different numerical values to calculate thresholds, separates the difference of the CT values in accordance with regions that are sorted by the thresholds, and thereby determines the certainty factor of the plaque region.

10. The plaque region extracting apparatus according to claim 5, wherein
the plaque extracting unit finds thresholds on the basis of a statistical analytic value of a pixel value in a required part of the blood vessel, and uses the thresholds to find plaque regions different in reliability.

11. The plaque region extracting apparatus according to claim 5, wherein
the image data is CT image data, and
the intermediate image data generating unit generates the second image data by filtering the intermediate region along the center line direction of the blood vessel included in the first image data,
the enhancement processing unit generates, from the difference of CT values between the first image data and the second image data, differential image data as the third image data in which image regions lower in the pixel value than peripheral portions are enhanced, and the enhancement processing unit generates, from the differential image data, a differential value distribution that indicates the number of pixels versus the difference of the CT values, and
the plaque extracting unit finds a standard deviation of the CT values from a required part of the blood vessel, integrally multiplies the standard deviation by different numerical values to calculate thresholds, separates the difference of the CT values in accordance with regions that are sorted by the thresholds, and thereby determines the certainty factor of the plaque region.

12. The plaque region extracting apparatus according to claim 11, wherein
the plaque extracting unit sets, as the thresholds, the standard deviation, double the standard deviation, and triple the standard deviation, and the plaque extracting unit unconditionally determines the difference of the CT values equal to or more than triple the standard deviation as the plaque region, determines the difference of the CT values between triple the standard deviation and double the standard deviation as the plaque region with a first condition, and determines the difference of the CT values between double the standard deviation and the standard deviation as the plaque region with a second condition.

13. The plaque region extracting apparatus according to claim 11, wherein
the first condition is to be adjacent to the unconditionally determined plaque region or to have a given volume or more, and
the second condition is to be adjacent to the determined plaque region.

* * * * *